US010456092B2

(12) United States Patent
Yamazaki

(10) Patent No.: US 10,456,092 B2
(45) Date of Patent: Oct. 29, 2019

(54) SURGICAL MICROSCOPE SYSTEM

(71) Applicant: MITAKA KOHKI CO., LTD., Tokyo (JP)

(72) Inventor: Toshio Yamazaki, Tokyo (JP)

(73) Assignee: MITAKA KOHKI CO., LTD., Tokyo (JP)

(*) Notice: Subject to any disclaimer, the term of this patent is extended or adjusted under 35 U.S.C. 154(b) by 25 days.

(21) Appl. No.: 15/877,761

(22) Filed: Jan. 23, 2018

(65) Prior Publication Data

US 2018/0206799 A1 Jul. 26, 2018

(30) Foreign Application Priority Data

Jan. 25, 2017 (JP) .................. 2017-011129

(51) Int. Cl.
| | |
|---|---|
| *G01B 11/25* | (2006.01) |
| *A61B 5/00* | (2006.01) |
| *G02B 21/00* | (2006.01) |
| *G01J 5/28* | (2006.01) |
| *G08B 21/18* | (2006.01) |
| *H04N 5/33* | (2006.01) |
| *A61B 90/30* | (2016.01) |
| *A61B 5/01* | (2006.01) |
| *G01J 5/00* | (2006.01) |

(Continued)

(52) U.S. Cl.
CPC .......... *A61B 5/746* (2013.01); *A61B 5/0077* (2013.01); *A61B 5/0082* (2013.01); *A61B 5/01* (2013.01); *A61B 5/015* (2013.01); *A61B 5/7275* (2013.01); *A61B 5/7405* (2013.01); *A61B 90/30* (2016.02); *G01J 5/28* (2013.01); *G02B 21/0012* (2013.01); *G08B 21/182* (2013.01); *H04N 5/33* (2013.01); *G01J 5/0066* (2013.01); *G01J 2005/0077* (2013.01); *G02B 21/025* (2013.01); *G16H 40/63* (2018.01)

(58) Field of Classification Search
CPC ....... A61B 5/746; A61B 5/015; A61B 5/7275; A61B 90/30; A61B 5/0082; A61B 5/7405; A61B 5/0077; A61B 5/01; H04N 5/33; G08B 21/182; G16H 50/30; G01J 2005/0077; G01J 5/0066; G01J 5/28; G02B 21/025; G02B 21/0012
See application file for complete search history.

(56) References Cited

U.S. PATENT DOCUMENTS

| | | | | |
|---|---|---|---|---|
| 8,190,243 | B2 * | 5/2012 | Welches | ............... A61B 18/201 600/474 |
| 2004/0174592 | A1 * | 9/2004 | Sander | ............... G02B 21/0012 359/388 |

(Continued)

FOREIGN PATENT DOCUMENTS

JP 2009-136578 A 6/2009

*Primary Examiner* — Howard D Brown, Jr.
(74) *Attorney, Agent, or Firm* — Greenblum & Bernstein, P.L.C.

(57) ABSTRACT

A surgical microscope system includes an infrared thermocamera that directly obtains temperature data on an illuminating spot. If the obtained temperature data indicates a higher temperature than a temperature represented by reference temperature data, an alarm unit generates an alarming sound to notify in advance a risk of overheating so that a counteraction such as stopping an illuminating beam can be taken to surely prevent the overheating of the illuminating spot.

9 Claims, 4 Drawing Sheets

(51) Int. Cl.
  *G02B 21/02*  (2006.01)
  *G16H 40/63*  (2018.01)

(56)  References Cited

U.S. PATENT DOCUMENTS

| | | | | |
|---|---|---|---|---|
| 2006/0087729 | A1* | 4/2006 | Oelckers | G02B 21/0012 359/388 |
| 2008/0049314 | A1* | 2/2008 | Steffen | G02B 6/4298 359/389 |
| 2010/0302629 | A1* | 12/2010 | Steffen | G02B 21/0012 359/385 |
| 2015/0300816 | A1* | 10/2015 | Yang | A61B 90/35 600/424 |
| 2017/0196453 | A1* | 7/2017 | Papac | G06F 3/0416 |
| 2018/0206799 | A1* | 7/2018 | Yamazaki | A61B 5/015 |

* cited by examiner

SURGICAL MICROSCOPE SYSTEM

BACKGROUND OF THE INVENTION

1. Field of the Invention

The present invention relates to a surgical microscope system capable of surely preventing an illuminating beam from excessively heating a surgical field and the periphery thereof.

2. Description of Related Art

An example of a surgical microscope for neurosurgery and the like is disclosed in, for example, Japanese Unexamined Patent Application Publication No. 2009-136578. The surgical microscope picks up light reflected from a surgical field through a light intake formed at a lower part of the surgical microscope and guides the picked-up light through an objective optical system and a variable power optical system to an eyepiece optical system to enable a stereoscopic observation of an optical image of the surgical field.

An illuminating beam is emitted from the vicinity of the light intake of the surgical microscope toward the surgical field to form an illuminating spot covering the surgical field. The illuminating beam increases the amount of light reflected from the surgical field to realize a secure observation of the surgical field. If the illuminating beam has high power and is emitted from a short distance, an area of the illuminating spot containing the surgical field will excessively be heated to raise a risk of causing a burn damage to the surgical field. To cope with this, the surgical microscope is provided with a safety mechanism that decreases the output of the illuminating beam if the surgical microscope is brought closer to the surgical field.

SUMMARY OF THE INVENTION

Although surgical microscopes of related arts are provided with safety mechanisms, a surgical microscope system capable of securing further safety is needed for the sake of protection during surgery.

In consideration of such a need, the present invention provides a surgical microscope system capable of surely preventing an illuminating beam from creating an excessively heated illuminating spot.

According to an aspect of the present invention, the surgical microscope system includes a surgical microscope that takes, through a light intake formed at a bottom part of the surgical microscope, light reflected from a surgical field into an objective optical system and guides the taken light passing through the objective optical system to a variable power optical system and then to an eyepiece optical system, an illuminating unit that emits an illuminating beam and forms an illuminating spot around the surgical field, the illuminating spot covering at least the surgical field, an infrared thermocamera that is attached to the surgical microscope, photographs a monitoring area containing at least the illuminating spot, and provides temperature data on the monitoring area, and an alarming unit that is activated if at least a data piece among the temperature data provided by the infrared thermocamera indicates a higher temperature than a temperature represented by reference temperature data.

DESCRIPTION OF PREFERRED EMBODIMENTS

Figure 1:
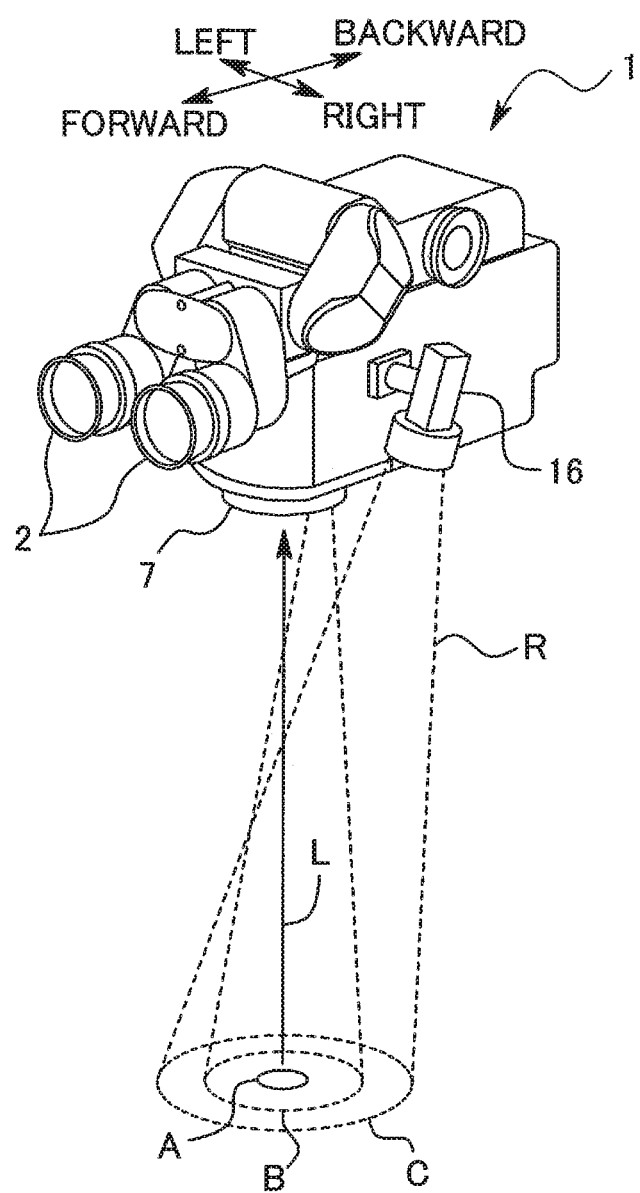
FIG. 1 is a perspective view illustrating a surgical microscope of a surgical microscope system according to a first embodiment of the present invention.
Figure 2:
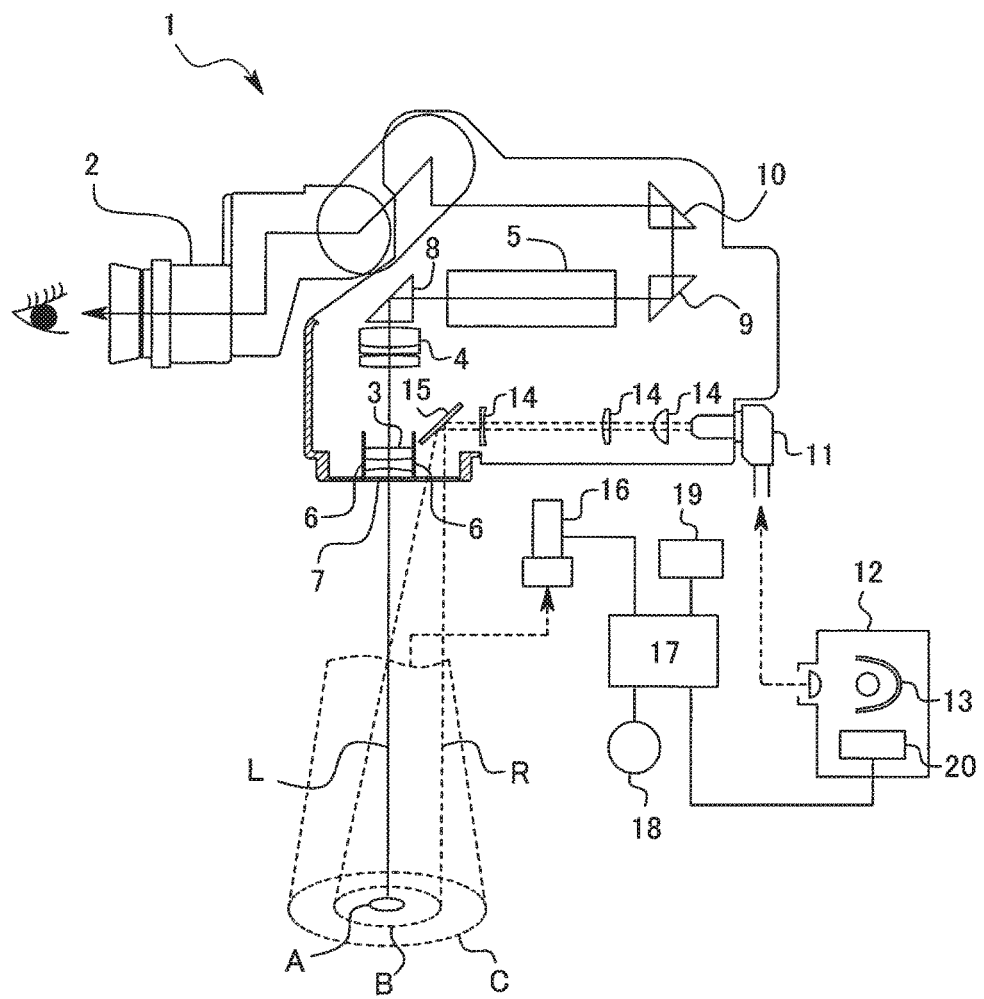
FIG. 2 is a sectional view illustrating the surgical microscope system according to the first embodiment.

FIGS. 1 and 2 illustrate a surgical microscope system according to the first embodiment of the present invention. Front, rear, left, and right directions illustrated in FIG. 1 are applicable to all drawings and explanations of this specification.

A surgical microscope 1 is supported with an arm of a stand apparatus (not illustrated) that is installed in an operation room. The surgical microscope 1 is a stereoscopic microscope having an eyepiece part (eyepiece optical system) 2 on the front side thereof. The surgical microscope 1 incorporates objective optical systems 3 and 4 in a vertical direction and a variable power optical system 5 in a horizontal direction. The objective optical systems 3 and 4 are vertically separated from each other to adjust a focal point. Each of the objective optical systems 3 and 4 has circular lenses whose front and rear parts are cut into a shape elongated in the left-right direction. The lower objective optical system 3 is provided with a douser 6 at each of the front and rear cut parts.

A bottom part of the surgical microscope 1 forms a light intake 7. Below the surgical microscope 1, there is a surgical field A to be observed with the surgical microscope 1. Light L reflected from the surgical field A is taken through the light intake 7 into the surgical microscope 1.

The light L taken through the light intake 7 is introduced into the objective optical systems 3 and 4 and is passed through a prism 8 to the variable power optical system 5. The light passed through the variable power optical system 5 is bent by lower and upper prisms 9 and 10 toward the eyepiece part 2. Between the prism 8 and the eyepiece part 2, there are a left-and-right pair of optical elements to realize a three-dimensional observation.

Connected to a rear face of the surgical microscope 1 is a light guide 11 to guide an illuminating beam R. The light guide 11 is connected through an optical fiber to an external light source unit 12. The light source unit 12 includes a xenon lamp 13 to emit the illuminating beam R that is introduced through the optical fiber and light guide 11 into the surgical microscope 1. The "illuminating unit" stipulated in the claims includes the light source unit 12 and light guide 11.

The illuminating beam R introduced into the surgical microscope 1 passes through three lenses 14 arranged in an introduction optical path, is reflected toward the surgical field A by an illuminating mirror 15 arranged behind the lower objective optical system 3, and forms an illuminating spot B covering the surgical field A. The illuminating beam R reflected by the illuminating mirror 15 spreads at a predetermined angle in a conical shape to illuminate the surgical field A. The illuminating spot B is larger than the surgical field A and illuminates the surgical field A and the periphery thereof. Since the illuminating mirror 15 is behind the objective optical system 3, the illuminating beam R slightly obliquely illuminates the surgical field A. The illuminating beam R to illuminate the surgical field A sufficiently secures the intensity of the light L reflected from the surgical field A into the surgical microscope 1 so that the eyepiece part 2 may realize a clear observation.

Attached to a right side face of the surgical microscope 1 is an infrared thermocamera 16. The infrared thermocamera 16 is oriented toward the illuminating spot B and photographs a monitoring area C that is larger than and covers the illuminating spot B. The infrared thermocamera 16 detects infrared radiation energy of the monitoring area C, measures temperatures from the detected energy, obtains data concerning a temperature distribution of the monitoring area C, and outputs the data to a controller 17.

The controller 17 is connected to, in addition to the infrared thermocamera 16, an alarm 18, a display 19, and a circuit board 20 of the light source unit 12. The display 19 displays a temperature distribution image of the monitoring area C according to the data from the infrared thermocamera 16. The alarm 18 generates, when activated, an alarming sound. According to the embodiment, the controller 17 and alarm 18 constitute the "alarming unit" stipulated in the claims.

The controller 17 stores in advance reference temperature data that is determined according to the surgical field A, a surgical operation to be carried out, and the like. The reference temperature data corresponds to a state before the surgical field A is overheated. Namely, the reference temperature data represents an upper limit of a safe temperature range for the surgical field A. If the upper limit temperature is exceeded, the illuminating spot B will grow into an overheated state.

If any data piece among the temperature data obtained from the monitoring area C exceeds the reference temperature data, the controller 17 activates the alarm 18 to generate an alarming sound. The alarming sound notifies the emergency immediately and simultaneously to anyone around the surgical microscope 1 to let them quickly cope with the emergency. The alarm 18 may adopt not only the alarming sound but also an alarming lamp, a flashing light, and the like.

If any data piece among the obtained temperature data exceeds the reference temperature data, the controller 17 issues a signal to the circuit board 20 of the light source unit 12, to automatically decrease the output of the illuminating beam R, thereby preventing the temperatures in the monitoring area C from further increasing. Instead of decreasing the output of the illuminating beam R, the controller 17 may stop the light source unit 12 from outputting the illuminating beam R.

According to the embodiment, the infrared thermocamera 16 is attached to an external part (a right side face) of the surgical microscope 1. This configuration allows the infrared thermocamera 16 to be attached to any existing surgical microscope without changing the internal structure of the surgical microscope.

Figure 3:
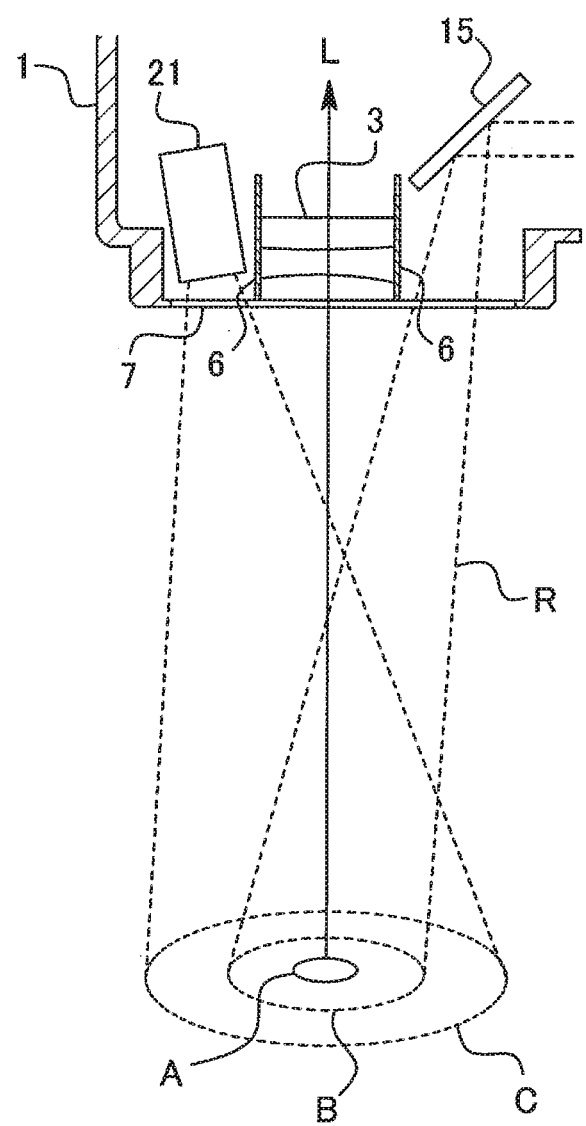
FIG. 3 is a sectional view illustrating the vicinities of a light intake of a surgical microscope system according to a second embodiment of the present invention.

FIG. 3 illustrates a surgical microscope system according to the second embodiment of the present invention. The second embodiment employs structural elements that are similar to those of the first embodiment, and therefore, like elements are represented with like reference marks to omit a repetition of their explanations.

According to the second embodiment, an infrared thermocamera 21 is installed inside the surgical microscope 1. The front and rear parts of the objective optical system 3 are cut to leave spaces in front of and behind the same. The space behind the objective optical system 3 is occupied by the illuminating mirror 15 and the space in front thereof is vacant. Accordingly, the second embodiment arranges the compact infrared thermocamera 21 in the vacant front space.

The infrared thermocamera 21 is set at an angle to see the surgical field A through the light intake 7 and obtain temperature data on the monitoring area C containing the illuminating spot B. Since the infrared thermocamera 21 is installed inside the surgical microscope 1, there is a free space on the side face of the surgical microscope 1 to accept another accessory in place of the infrared thermocamera.

Figure 4:
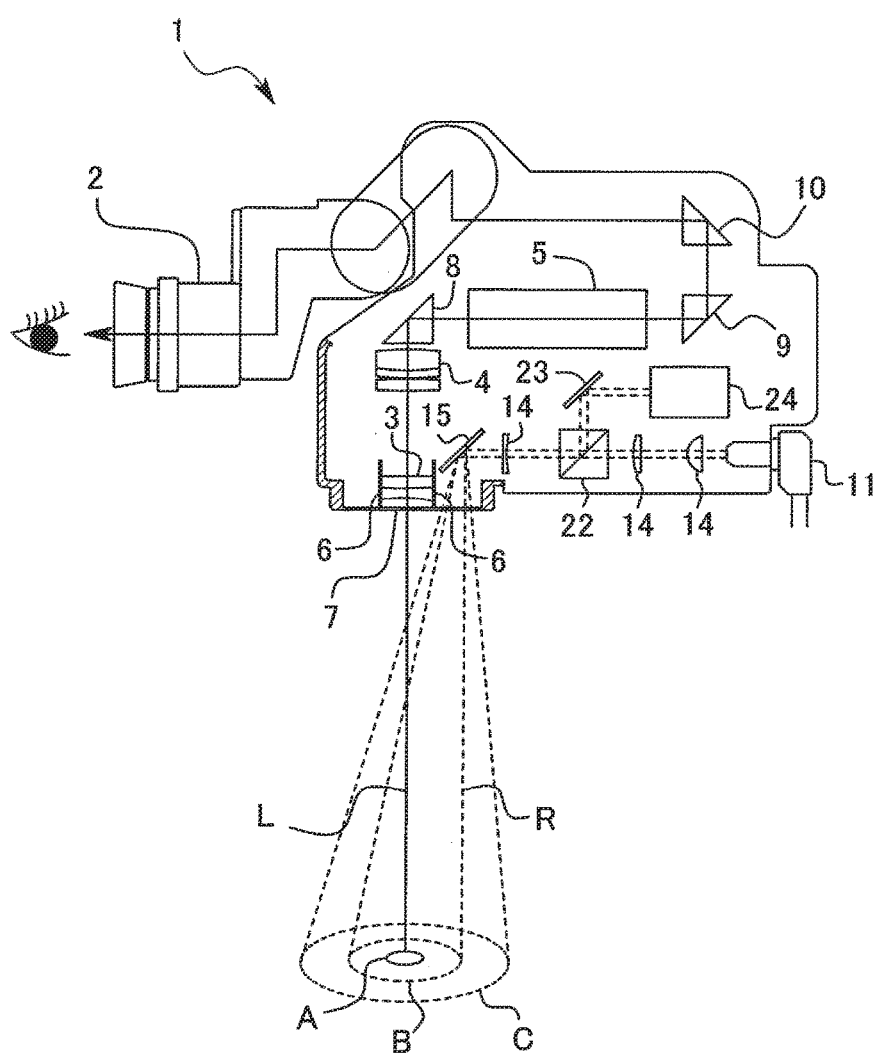
FIG. 4 is a sectional view illustrating a surgical microscope system according to a third embodiment of the present invention.

FIG. 4 illustrates a surgical microscope system according to the third embodiment of the present invention.

In the introduction optical path for the illuminating beam R inside the surgical microscope 1, the third embodiment arranges a beam splitter 22. Above the beam splitter 22, a reflection mirror 23 is arranged, and behind the reflection mirror 23, an infrared thermocamera 24 is arranged.

An infrared beam coming from the entire monitoring area C is reflected by the illuminating mirror 15 into the introduction optical path of the illuminating beam R in a direction opposite to an advancing direction of the illuminating beam R. Part of the infrared beam advancing opposite to the illuminating beam R is branched by the beam splitter 22, is reflected by the reflection mirror 23, and is guided into the infrared thermocamera 24. Namely, the infrared thermocamera 24 photographs the monitoring area C through the illuminating mirror 15. An optical axis of the illuminating beam R agrees with an optical axis of the infrared beam. Accordingly, even if the angle of the illuminating mirror 15 is changed, the monitoring area C always contains the illuminating spot B. Sensitivity of the infrared thermocamera 24 is adjusted in advance in consideration of the partial branching of the infrared beam by the beam splitter 22, to correctly measure temperatures in the monitoring area C.

According to the third embodiment, the infrared thermocamera 24 photographs the monitoring area C through the illuminating mirror 15 that serves as an illumination start point. Accordingly, the infrared thermocamera 24 is able to photograph an entire range of the illuminating beam R that spreads in a conical shape from the illuminating mirror 15 toward the illuminating spot B. If something enters into upper part of the illuminating beam R, the third embodiment is able to detect a heated (or overheated) state of the entered thing. Even if the entered thing does not demonstrate a heated state, the infrared thermocamera 24 is able to provide a thermal image including the entered thing, and therefore, one can notice the existence of the entered thing.

In summary, a first aspect of the present invention attaches an infrared thermocamera to a surgical microscope to directly obtain temperature data on an illuminating spot formed by an illuminating beam, and if any data piece among the obtained temperature data indicates a higher temperature than a temperature represented by reference temperature data, activates an alarming unit. The reference temperature data is set in advance according to an illuminating unit of the surgical microscope and a surgical operation to be carried out, to secure safety and let anyone know beforehand a risk of exceeding the reference temperature data. If such a risk is sensed, the illuminating unit is stopped or its output is decreased to surely prevent any part in the illuminating spot from being excessively heated.

A second aspect of the present invention makes the alarming unit generate an alarming sound if the above-mentioned risk is detected. The alarming sound notifies the emergency immediately and simultaneously to anyone around the surgical microscope and lets them quickly cope with the emergency.

A third aspect of the present invention attaches the infrared thermocamera to an external part of the surgical microscope. Namely, without changing the internal structure of any existing surgical microscope, the infrared thermocamera is attachable to the existing surgical microscope.

A fourth aspect of the present invention installs the infrared thermocamera inside the surgical microscope. This configuration allows an accessory other than the infrared thermocamera to be attached to the external part of the surgical microscope.

According to a fifth aspect of the present invention, the infrared thermocamera installed inside the surgical microscope picks up images through an illuminating mirror that serves as an illumination start point of the illuminating beam. As a result, the infrared thermocamera is able to photograph not only a monitoring area that covers the illuminating spot but also an entire range of the illuminating beam that spreads in a conical shape from the illuminating mirror to the illuminating spot. This configuration is capable of detecting a heated (or overheated) state not only of the monitoring area but also of a thing that enters into upper part of the illuminating beam.

This patent application claims the benefit of priority under 35 U.S.C. 119(a) to Japanese Patent Application No. 2017-011129 filed on Jan. 25, 2017 whose disclosed contents are cited herein.

What is claimed is:

1. A surgical microscope system comprising:
    a surgical microscope taking light reflected from a surgical field into an objective optical system through a light intake formed at a bottom part of the surgical microscope, and guiding the taken light passing through the objective optical system through a variable power optical system to an eyepiece optical system;
    an illuminating unit emitting an illuminating beam and forming an illuminating spot around the surgical field, the illuminating spot covering at least the surgical field;
    an infrared thermocamera attached to the surgical microscope, imaging a monitoring area containing at least the illuminating spot, and providing temperature data on the monitoring area; and
    an alarming unit being activated if at least a data piece among the temperature data provided by the infrared thermocamera indicates a higher temperature than a temperature represented by reference temperature data,
    wherein the monitoring area of the infrared thermocamera is larger than the surgical field and the illuminating spot, and the illuminating spot is larger than the surgical field.

2. The surgical microscope system of claim 1, wherein the alarming unit generates an alarming sound.

3. The surgical microscope system of claim 1, wherein the infrared thermocamera is attached to an external part of the surgical microscope.

4. The surgical microscope system of claim 1, wherein the infrared thermocamera is attached to an internal part of the surgical microscope and images the monitoring area through the light intake.

5. The surgical microscope system of claim 4, wherein:
    the illuminating unit is configured to reflect an illuminating beam, which is introduced from a light source into the surgical microscope, with an illuminating mirror, which is arranged at an end of the objective optical system, and form the illuminating spot covering the surgical field; and
    the infrared thermocamera is configured to photograph through the illuminating mirror the monitoring area and an entire range of the illuminating beam between the illuminating mirror and the illuminating spot.

6. A surgical microscope system comprising:
    a surgical microscope taking light reflected from a surgical field into an objective optical system through a light intake formed at a bottom part of the surgical microscope, and guiding the taken light passing through the objective optical system through a variable power optical system to an eyepiece optical system;
    an illuminating unit emitting an illuminating beam and forming an illuminating spot around the surgical field, the illuminating spot covering at least the surgical field;
    an infrared thermocamera attached to the surgical microscope, imaging a monitoring area containing at least the illuminating spot, and providing temperature data on the monitoring area; and
    an alarming unit being activated if at least a data piece among the temperature data provided by the infrared thermocamera indicates a higher temperature than a temperature represented by reference temperature data,
    wherein the optical axis of the illuminating beam is the same as the optical axis of the infrared beam.

7. A surgical microscope system comprising:
    a surgical microscope taking light reflected from a surgical field into an objective optical system through a light intake formed at a bottom part of the surgical microscope, and guiding the taken light passing through the objective optical system through a variable power optical system to an eyepiece optical system;
    an illuminating unit emitting an illuminating beam and forming an illuminating spot around the surgical field, the illuminating spot covering at least the surgical field;
    an infrared thermocamera attached to the surgical microscope, imaging a monitoring area containing at least the illuminating spot, and providing temperature data on the monitoring area;
    an alarming unit being activated if at least a data piece among the temperature data provided by the infrared thermocamera indicates a higher temperature than a temperature represented by reference temperature data;
    an illuminating mirror reflecting the illuminating beam to the surgical field;
    a beam splitter reflecting infrared light and passing the illuminating beam therethrough, and located
        in the path of a light source producing the illuminating beam to pass the illuminating beam therethrough to the illuminating mirror, and
        in the path of infrared light from the surgical spot and reflected by the illuminating mirror toward the beam splitter; and
    a reflection mirror reflecting the infrared light reflected by the beam splitter from the surgical field to the thermocamera, and
    wherein the thermocamera is located to receive the infrared light reflected by the reflection mirror.

8. The surgical microscope system of claim 1, further comprising an illuminating mirror reflecting the illuminating beam to the surgical field, wherein the thermocamera photographs the monitoring area by receiving infrared light from the surgical field reflected by the illuminating mirror.

9. The surgical microscope system of claim 1, further comprising:

an illuminating mirror reflecting the illuminating beam to the surgical field; and
a beam splitter, reflecting infrared light and passing the illuminating beam therethrough, the beam splitter being located
 in the path of a light source producing the illuminating beam to pass the illuminating beam therethrough to the illuminating mirror, and
 in the path of infrared light from the surgical spot and reflected by the illuminating mirror toward the beam splitter, and
wherein the thermocamera is located to receive the infrared light reflected by the beam splitter.

* * * * *